US010500182B2

(12) United States Patent
Firger et al.

(10) Patent No.: US 10,500,182 B2
(45) Date of Patent: Dec. 10, 2019

(54) COMPOSITIONS OF KETOGENIC SOURCES, MICRONUTRIENTS AND PHYTOCHEMICALS FOR PROPHYLAXIS AND MITIGATION OF MIGRAINE HEADACHE

(71) Applicants: Robert Firger, Bloomfield, CT (US); Gerald Haase, Denver, CO (US)

(72) Inventors: Robert Firger, Bloomfield, CT (US); Gerald Haase, Denver, CO (US)

( * ) Notice: Subject to any disclaimer, the term of this patent is extended or adjusted under 35 U.S.C. 154(b) by 0 days.

(21) Appl. No.: 16/501,249

(22) Filed: Mar. 13, 2019

(65) Prior Publication Data

US 2019/0209491 A1 Jul. 11, 2019

Related U.S. Application Data

(63) Continuation-in-part of application No. 15/743,448, filed on Jan. 10, 2018, now abandoned.

(51) Int. Cl.

| | |
|---|---|
| ***A61K 36/00*** | (2006.01) |
| ***A61K 31/23*** | (2006.01) |
| ***A61K 36/28*** | (2006.01) |
| ***A61K 36/889*** | (2006.01) |
| ***A61P 25/06*** | (2006.01) |
| ***A61K 31/12*** | (2006.01) |
| ***A61K 31/122*** | (2006.01) |
| ***A61K 31/22*** | (2006.01) |
| ***A61K 31/341*** | (2006.01) |
| ***A61K 31/355*** | (2006.01) |
| ***A61K 31/4045*** | (2006.01) |
| ***A61K 31/4415*** | (2006.01) |
| ***A61K 31/522*** | (2006.01) |
| ***A61K 31/525*** | (2006.01) |
| ***A61K 31/7084*** | (2006.01) |
| ***A61K 33/06*** | (2006.01) |
| ***A61K 36/35*** | (2006.01) |
| ***A61K 36/53*** | (2006.01) |
| ***A61K 36/534*** | (2006.01) |
| ***A61K 36/9068*** | (2006.01) |

(52) U.S. Cl.

CPC .............. *A61K 31/23* (2013.01); *A61K 31/12* (2013.01); *A61K 31/122* (2013.01); *A61K 31/22* (2013.01); *A61K 31/341* (2013.01); *A61K 31/355* (2013.01); *A61K 31/4045* (2013.01); *A61K 31/4415* (2013.01); *A61K 31/522* (2013.01); *A61K 31/525* (2013.01); *A61K 31/7084* (2013.01); *A61K 33/06* (2013.01); *A61K 36/28* (2013.01); *A61K 36/35* (2013.01); *A61K 36/53* (2013.01); *A61K 36/534* (2013.01); *A61K 36/889* (2013.01); *A61K 36/9068* (2013.01); *A61P 25/06* (2018.01)

(58) Field of Classification Search

None

See application file for complete search history.

(56) References Cited

U.S. PATENT DOCUMENTS

| | | | | |
|---|---|---|---|---|
| 2012/0177732 A1* | 7/2012 | Buckley | .................. | A61K 9/14 424/455 |
| 2013/0203701 A1* | 8/2013 | Leighton | ................ | A61K 31/20 514/62 |
| 2015/0132440 A1* | 5/2015 | Owoc | ....................... | A23L 2/66 426/73 |
| 2015/0342974 A1* | 12/2015 | Chow | .................. | A61K 31/702 514/61 |

* cited by examiner

*Primary Examiner* — Qiuwen Mi

(74) *Attorney, Agent, or Firm* — Dan De La Rosa

(57) ABSTRACT

A formulation comprising at least one ketogenic source, at least one vitamin, at least one mineral, at least one antioxidant, optionally at least one phytonutrient, and optionally at least one other nutrient, and mixtures and combinations thereof intended for the prevention and mitigation of migraine headache.

2 Claims, No Drawings

COMPOSITIONS OF KETOGENIC SOURCES, MICRONUTRIENTS AND PHYTOCHEMICALS FOR PROPHYLAXIS AND MITIGATION OF MIGRAINE HEADACHE

RELATED APPLICATIONS

This is a Continuation-in-Part of U.S. application Ser. No. 15/743,448 entitled "Prophylaxis and mitigation of migraine headaches using medium chain triglycerides, ketone esters, and other ketogenic sources", filed on Jan. 10, 2018, which has now been granted a Notice of Allowance, which is related to Provisional Application Ser. No. 62/191,075 filed on Jul. 10, 2018.

FIELD OF THE INVENTION

The invention relates to migraine headaches, sometimes simply called migraine. This invention relates to methods and formulations of ketogenic sources including medium chain triglycerides and ketone esters, micronutrients including vitamins, minerals and antioxidants, phytonutrients from herbs, plants or their derivatives, and other nutrients for preventing, arresting or reducing the frequency or severity of migraine headache.

SUMMARY OF THE INVENTION

Migraine is a neurological disease with a strong genetic component. It is characterized by episodes of disabling headache, often called migraine attacks. They are clinically quite different from regular headaches which are non-migrainous. There are about 100 million people with headaches in the U.S., about 37 million of these people have migraines. The World Health Organization estimates that approximately 18 percent of women and 7 percent of men in the U.S. suffer from migraines. People who suffer from migraine are known as "migraineurs". Migraine ranks in the top 20 of the world's most disabling medical illnesses. (See Global Burden of Disease Study, updated 2004, World Health Organization)

Migraines are called primary headaches because the pain isn't caused by another disorder or disease such as a brain tumor or head injury. Some cause pain on just the right side or left side of the head (hemicrania), others result in generalized head pain. Migraine sufferers may have moderate or severe pain and usually can't participate in normal activities, during the duration of the attack, because of the pain. Often when a migraine strikes, people can't think beyond trying to find a quiet, dark room. More than 90% of sufferers are unable to function normally during their migraine attacks. Because of migraine-induced disability, American employers lose more than $13 billion each year as a result of 113 million lost work days.

Many people experience migraine attacks lasting for at least four hours and which may last for days. The range of time someone is affected by an attack is actually longer than the full-blown attack itself, as there is a pre-monitory, or build-up phase, and a post-dromal phase that can last one to two days. An estimated 14 million individuals in the U.S. are classified as "chronic migraneurs", meaning that they suffer a migraine episode a minimum of 15 days each month. For all intents and purposes, this means that with migraine symptoms usually lasting multiple days, these sufferers may experience the impact of migraine on their lives virtually every day.

Recent research has highlighted the potential importance of neurogenic inflammation in migraine pathophysiology and pharmacology. Extravasation (inflammatory leakage of white blood cells from the capillaries), vasodilatation (widening of blood vessels resulting in lowered blood pressure), mast cell activation, and the release of pro-inflammatory mediators may activate trigeminal afferents (the nerve fibers of the fifth cranial nerve governing sensation in the face and certain facial motor activity), thus leading to sensitization in the migraineur. There are indications that blockading vasodilatation in inflammation may be effective in the treatment of migraine. It has been shown that the ketone body 3-hydroxybutyrate has beneficial effects on inflammation, with significant potential for addressing aspects of a variety of metabolic related diseases.

A number of different medications have been used to treat migraine, with varying levels of effectiveness. All of these treatments, however, with increased frequency of use can lead to a condition called medication overuse headache (MOH). Medication-overuse headaches occur when medications not only stop relieving pain but themselves also cause headaches. Patients then use more pain medication, which may lengthen the duration of pain of the migraine sufferer. In addition, these treatments pose additional, specific risks such as drug sensitivities, cognitive symptoms and negative physiological effects, some of which are further elucidated below.

For pain associated with mild or moderate migraine, aspirin or non-steroidal anti-inflammatory drugs (NSAIDs, such as ibuprofen and naproxen) are commonly used. Unfortunately, regular use of these medications can result in abdominal pain and intestinal ulcers-often associated with hemorrhage, and they are generally not effective against more severe migraine.

Front-line treatments for more severe migraine include the triptans, such as sumatriptan (Imitrex), rizatriptan (Maxalt), almotriptan (Axert), naratriptan (Amerge), zolmitriptan (Zomig), frovatriptan (Frova) and eletriptan (Relpax). In addition to MOH, these medications can cause a condition called "serotonin syndrome" when used together with selective serotonin reuptake inhibitors (SSRIs), including Prozac, Celexa, Luvox, Zoloft, Paxil and Lexapro; or serotonin and norepinephrine inhibitors (SNRIs), including Effexor, Pristiq and Cymbalta, all of which are commonly prescribed for depression and/or anxiety. These are mental health conditions for which migraneurs already may be receiving treatment with some frequency. The front-line medications, discussed above, are often serotonin agonists whose nature it is to raise serotonin levels. When taken in combination, they can cause serotonin levels in the CNS (central nervous system) to rise to especially high levels. "Serotonin syndrome" is a rare, potentially life-threatening condition that occurs when an excess of serotonin—a neurotransmitter of major importance in the central nervous system (CNS) accumulates in the brain.

Less effective than triptans are ergotamines, such as ergotamine and dihydroergotamine. Ergotamines appear to be most useful for people who have migraines that last a long period of time, but don't have frequent migraine attacks. Side effects of ergotamines include dizziness, nausea and vomiting, cold, clammy hands and feet, muscle pain, numbness, and feelings of discomfort or anxiety. Ergotamines also can have serious interactions with a large number of drugs.

Medications containing narcotics, particularly codeine, are sometimes used to treat migraine headache pain for people who can't take triptans or ergotamines. Narcotics are seriously habit-forming and are usually used only as a last resort.

Glucocorticoids, such as prednisone and dexamethasone may be used in conjunction with other medications to improve pain relief Because of the risk of adverse side effects, glucocorticoids should not be used frequently or for prolonged periods, which presents problems for chronic migraneurs.

Due to the severity and frequency of the side effects caused by many of these medications that treat symptoms of migraine, another strategy is to utilize medications that reduce the frequency of migraine attacks.

One front line treatment for reducing frequency of migraine onsets is beta blockers, which are normally and usually prescribed for high blood pressure and heart problems. Unfortunately, beta blockers produce their own, often severe side effects, including fatigue, nausea, reduced ability to exercise, insomnia, sleep problems, nightmares and vivid dreams, memory problems, depression, weight gain, and exacerbation of asthma.

Calcium channel blockers, which are also normally prescribed for high blood pressure and heart problems, are sometimes prescribed to reduce frequency of migraine onset. However, these drugs carry their own side effect profile, including dizziness, drowsiness, constipation, nausea, headache, rash, pitting edema of the feet, ankles and lower legs (owing to water retention), low blood pressure, tachycardia (rapid heartbeat), and flushing (reddening) of the face, neck and/or upper chest.

Tricyclic antidepressants are sometimes used to reduce frequency of migraine onset. Unfortunately, these drugs have a wide range of undesirable side effects, including disturbances in heart rhythm, increased sensitivity to sunlight, drowsiness, dry mouth, painful urination, sexual dysfunction, weight gain, dizziness, lightheadedness, and headaches. In addition, antidepressants come with the U.S. Food and Drug Administration's strongest "black box" warning that the use of antidepressants has been associated with an increased risk of suicidal thoughts and behaviors in children, adolescents and young adults. Tricyclic antidepressants can be fatal in overdose.

Anticonvulsants are sometimes prescribed to reduce frequency of migraine onset. Only Depakote (gen. valproic acid) and Topamax (gen. topiramate) have been approved for this purpose. However, some anticonvulsant medications may reduce the effectiveness of oral contraceptives, since their induction of the hepatic cytochrome P450 (CYP450) isoenzyme causes decreased sex hormone levels in women taking oral contraceptives, thus raising the potential for decreased effectiveness of oral contraceptives and increased risk of unplanned pregnancy. In addition, more than half of people who take anticonvulsant drugs report experiencing at least one side effect, the most common of which are dizziness, nausea and sleepiness. Some people who take newer drugs in this class also experience swelling in the feet and hands, weight gain, blurry vision, trouble concentrating, and lapses in memory.

More recently, injections of botulinum toxin (Botox®) have been used to reduce frequency of migraine onset. However, Botox's side effects include headache, facial loss of movement, eyelid drooping, lung inflammation, neck pain, muscle stiffness and weakness, muscle pain and spasms, pain at injection site, and high blood pressure. In addition, the paralyzing effect of Botox can spread to other areas of the body and can cause general weakness, double vision, difficulty swallowing, voice and speech disorders, loss of bladder control and difficulty breathing.

Given the frequency and severity of side effects of both medications to treat symptoms of migraine and to reduce frequency of migraine onset, there clearly is a need for safer treatments to prevent or reduce frequency of migraine onset and reduce migraine symptoms. However, some authors have described ketogenic dieting as potentially causing severe headaches, and low glucose levels, among a number of other physiological effects of ketogenic dieting, which might complicate its use. In addition, adherence to a ketogenic diet can be difficult and compliance problems frequently arise.

The present invention provides for a series of complex nutrient formulations and combinations comprising medium chain triglycerides, coconut oil extracts, ketone salts/esters, vitamin B2, vitamin B3, vitamin B6, vitamin C, vitamin E, magnesium, co-enzyme Q-10, basil oil, butterbur, feverfew, ginger root, peppermint extract, valerian, caffeine, melatonin for consumption and peppermint oil for application to the skin wherein said formulations are designed for protection against the onset of migraine headache as well as to reduce its symptom frequency, severity and adverse impact on quality of life in humans. The rationale for the multiple compositions and the ingredients excluded is explained and the primary target dosage schedule with acceptable dose ranges is provided.

The invention provides effective, safer treatments to prevent or reduce frequency of migraine onset and reduce migraine symptoms. The present inventors have surprisingly discovered that providing KMCT to patients suffering from frequent migraine attacks can reduce frequency of migraine onset and reduce migraine symptoms, without the side effects of medications currently used for this purpose. KMCT are metabolized in the liver to provide a rich source of ketone bodies, which can be metabolized as a carbon and energy source for the body, especially the brain. Unlike ketogenic dieting, providing exogenous KMCT does not result in reduced glucose concentrations or other physiological effects associated with ketogenic dieting, and does not suffer from similar patient compliance issues. Ingestion of KMCT has no reported serious side effects and only minor and transitory reported effects of gastro-intestinal distress or sensitivity in some users, which has been shown to usually diminish with continued use.

In one embodiment, the present invention relates to a formulation comprising at least one ketogenic source, at least one vitamin, at least one mineral, at least one antioxidant, and mixtures and combinations thereof. In another embodiment, the formulation further comprises at least one phytonutrient and at least one nutrient. In still another embodiment, the ketogenic source is selected from a group comprising medium chain triglycerides, coconut oil, coconut capsule, palm capsule, medium chain triglyceride oils, caprylic acid, capric acid, medium chain triglyceride powder, coconut oil extracts, caproic acid, lauric acid, ketone salts, ketone esters, and mixtures and combinations thereof. In yet another embodiment, the vitamin is selected from a group comprising Vitamin B2, riboflavin, yeast, Vitamin B3, niacinamide ascorbate, nicotinic acid, nicotinamide riboside, nicotinamide adenine dinucleotide, vitamin B6, pyridoxine hydrochloride, and mixtures and combinations thereof. In still yet another embodiment, the mineral is selected form a group comprising magnesium citrate, magnesium lactate, magnesium gluconate, magnesium oxide, magnesium carbonate, magnesium hydroxide, magnesium chloride, magnesium sulphate, lactic acid, Jay phosphate, tribasic phosphate, natural form, and mixtures and combinations thereof. In a further embodiment, the antioxidant is selected from a group comprising Vitamin C, ascorbate salts, acidic form, citrus, rose, berry source, Vitamin E, vegetable products, wheat germ products, natural tocopherol, d-alpha tocopheryl succinate, d-alpha tocopheryl acetate, Coenzyme Q10, ubiquinone, organ meat, natural ingredient sources, *Agrobacterium tumefaciens, Paracoccus denitrificans, Pseudomonas aeruginosa*, and mixtures or combinations thereof. In yet a further embodiment, the phytonutrients are selected from a group comprising basil, butterbur, feverfew, ginger, peppermint, valerian, and mixtures and combinations thereof. In still a further embodiment, the nutrients are selected from a group comprising melatonin, caffeine, peppermint essential oil, and mixtures and combinations thereof.

In another embodiment, the ketogenic sources comprise 5 gms of medium chain triglycerides, 15 gms of medium chain triglyceride oils, 4 gms medium chain triglyceride powder, 20 gms of coconut oil extracts, and 25 gms of ketone salts/extracts. In yet another embodiment, the vitamins comprise 4 mg of Vitamin B2, 320 mg of forms of Vitamin B3, and 5 mg of Vitamin B6. In still another embodiment, the minerals comprise 300 mg of magnesium. In still yet another embodiment, the antioxidants comprise 500 mg of Vitamin C, 300 IU of Vitamin E, and 60 mg of Coenzyme Q10. In a further embodiment, the phytonutrients comprise 2000 mg of basil, 100 mg of butterbur, 500 mg of forms of feverfew, 500 mg of ginger, 100 mg of peppermint, and 250 mg of valerian. In another further embodiment, the nutrients comprise 3 mg of melatonin, 125 mg of caffeine, and 0.5 ml peppermint essential oil.

In another further embodiment, the present invention relates to a composition comprising: Medium chain triglycerides (coconut/palm, capsule or oil) from about 1 to about 30 grams; Medium chain triglyceride oil (caprylic, capric acids) from about 5 to about 50 grams; Medium chain triglyceride powder from about 1 to about 20 grams; Coconut oil extracts (caproic, caprylic, capric, lauric acids) from about 10 to about 50 grams; Ketone salts/esters from about 5 to about 60 grams; B2 (riboflavin, yeast source) from about 2 to about 400 mg; B3 (niacinamide ascorbate, nicotinic acid, yeast source) from about 5 to about 30 mg; B3 (nicotinamide riboside, nicotinamide adenine dinucleotide) from about 50 to about 2000 mg; B6 (pyridoxine hydrochloride, yeast source) from about 1 to about 50 mg; Magnesium (citrate, lactate, gluconate, oxide, carbonate, hydroxide, chloride, sulphate, lactic acid, Jay phosphate, tribasic phosphate, natural form) from about 50 to about 500 mg; Vitamin C (ascorbate salts/acidic form, citrus, rose, berry source) from about 100 to about 2000 mg; Vitamin E (vegetable, wheat germ products, natural tocopherol) (d-alpha tocopheryl succinate) from about 50 to about 400 IU; Vitamin E (d-alpha tocopheryl acetate) from about 25 to about 200 IU; Coenzyme Q10 (ubiquinone, organ meat or natural ingredient sources—e.g. *Agrobacterium tumefaciens, Paracoccus denitrificans, Pseudomonas aeruginosa*) from about 5 to about 250 mg; Basil (oil, extract, plant form) from about 500 to about 5000 mg; Butterbur from about 25 to about 200 mg; Feverfew (Parthenolides—standardized 0.2-0.4%, tea, leaves) from about 100 to about 1200 mg, Feverfew (carbon dioxide, extract) from about 5 to about 400 mg; Ginger (gingerol, root, tea, oil, powder) from about 50 to about 2,000 mg; Peppermint (extract, gel, liquid, chewable, enteric-coated, capsule) from about 50 to about 1000 mg; Valerian (root, tea, extract, powder, plant source) from about 100 to about 1200 mg; Melatonin (hormone, solid, liquid) from about 0.1 to about 10 mg; Caffeine from about 25 to about 250 mg; and Peppermint (essential oil-10% solution) from about 0.1 to about 1.5 ml.

In a further embodiment, the present invention provides for a method of manufacturing a formulation, and the method comprising admixing at least one ketogenic source, at least one vitamin, at least one mineral, at least one antioxidant, and mixtures and combinations thereof in varying amounts. In another further embodiment, the method further comprises admixing at least one phytonutrient, at least one nutrient, and mixtures and combinations thereof in varying amounts.

In yet another further embodiment, the formulation is utilized to treat, prevent, and relieve the symptoms of a migraine headache.

All categories of ingredients and ingredient sources herein are illustrative only and may include named ingredients, whether or not proprietary to the current invention, as well as alternative sources and iterations of such ingredients and ingredient categories, which may be substituted, added or may be novel to the present invention.

BACKGROUND OF THE INVENTION

Migraine headache is a primary disorder unrelated to another condition such as an injury or malignancy. Sufferers usually can't participate in normal activities during an attack because of the intensity of the pain. It is estimated that more than 100 million work days and $13 billion are lost annually, in the U.S. alone, due to migraine-induced disability. The duration of attacks lasts for hours to days and with about 14 million sufferers or "chronic migraineurs" being affected for a minimum of 15 days per month. Because migraine has such a long and pandemic global history of documented occurrence, a vast array of remedies preceded the development of modern pharmaceutical interventions. These included nutritional, herbal and plant-based ingredients, some of which provided documented beneficial effects.

Common dietary food items were often employed. For example, salmon, (balanced omega 3-6-9 fatty acid profile to combat inflammation), figs (high in potassium combined with other electrolytes), shrimp (astaxanthin-antioxidant and anti-inflammatory), as well as carrots, sweet potato, kale and collard greens (high carotenoid and phytochemical content) have been consumed in hopes of mitigating migraine headache. While not a formal part of the current invention, these foods are recommended as adjunctive measures for migraineurs to utilize. In this invention, certain herbals and other nutrients are included because they are highly effective, although their mechanisms of action may not yet be fully elucidated. Many of these plant-based therapies have proven to be efficacious both in validated clinical experience as well as in some peer-reviewed human trials. Those with the most durable benefits have been incorporated and include basil, butterbur, ginger, feverfew, mints (*mentha* spp.) and valerian.

In selecting herbals and phytonutrients, the inventors considered documented experiential evidence relative to migraine headache. The following nutrients were examined but specifically excluded because they ultimately had less scientific support and justification for their efficacy or may have represented particular safety concerns: coriander seed (*Coriandrum sativum*), with anti-inflammatory potential, lavender oil (*Lavandula angustifolia*) inhalation thought to promptly relieve symptoms, rosemary (*Rosmarinus officinalis*), linden, lime tree (*Tilia* spp.), horseradish (*Armoracia rusticana*) with vascular narrowing properties, honeysuckle (*Lonicera japonica*) with anti-inflammatory pain relief, yarrow (*Achillea millefolium*), teaberry (*Gaultheria procumbens*, "wintergreen") with potential to treat neuralgias, hops (*Humulus lupulus*), with sedative effects, betony (*Stachys officinalis*), to relieve facial swelling and pain, boswellia (Indian frankincense) with AKBA, turmeric, with anti-inflammatory curcuminoids, and willow (*Salix* spp.), with anti-inflammatory salicin.

To construct the most appropriate formulation to impact migraine headache, the dominant mechanisms of action had to be addressed. Neurogenic inflammation, vascular dilation and cytokine release are among those that impact migraine pathophysiology and pharmacology and represent potential therapeutic targets. Relative to the current invention, the ketone body, 3-hydroxybutyrate has shown beneficial effects by reducing inflammation. This is important because most treatments lose efficacy with increased use over time while often causing adverse side effects. These therapies and their problematic accompanying effects are well described in the related "parent" patent to this "continuation-in-part" application. The rather extensive list includes non-steroidal anti-inflammatory drugs, narcotic analgesics, steroids, beta blockers, triptans, serotonergic agents, calcium channel blockers, ergotamines, tricyclic antidepressants, anticonvulsants, and occasionally in desperation, botulinum toxin. These compounds have also been excluded from this invention. Most recently, three pharmaceutical classes have been in development for migraine including calcitonin gene-related peptide (CGRP) inhibitors, gepants (oral CGRP receptor antagonists) and ditans (serotonin 5-HT receptor agonists). These new drugs are very expensive and current trials have shown at best only modest effect while the long-term safety profiles have in no manner been ascertained.

These realities added to the daunting spectrum of severe side effects from current treatment approaches clearly demonstrate the need for safer therapies to prevent or reduce frequency of migraine onset and minimize symptoms. Ketogenesis has been proposed as a beneficial strategy for migraineurs but adherence to a true ketogenic diet can be challenging. Another path is possible since providing KMCT to sufferers can reduce frequency of migraine onset and symptoms. The KMCT may comprise a mixture of capric and caprylic triglycerides and/or are enriched or purified from coconut oil as a parent source. KMCT are metabolized in the liver to provide a rich supply of ketone bodies, which can be metabolized as a carbon and energy source for the body, especially the brain. Providing exogenous KMCT does not result in adverse physiological effects or compliance issues associated with ketogenic dieting. Ingestion of KMCT has no reported serious side effects and only transitory gastro-intestinal distress or sensitivity in some users is noted. Thus, this approach can prevent or reduce the frequency of migraine headache onset, reduce symptom severity and augment benefits from other pharmaceutical (e.g. as listed previously in this section) or non-pharmaceutical interventions (e.g. such as some agents included in this formulation listed in a subsequent section). In addition, dietary ketones can be provided by ketone esters, ketone salts and/or combinations thereof and raise plasma ketone body levels to clinically effective ranges.

Two factors further contributing to the severity of the migraine headache issue are oxidative stress and inflammation. Oxidative damage from excess free radicals is generated by normal metabolism including neuro-physiological and hormonal stress, as well as a diverse number of external factors affecting human health including air pollution, occupational exposures, physical activity, radiation and smoking. This oxidative stress may injure cells, tissues, organs and body proteins, lipids and DNA. If they damage non-dividing cells such as neurons, it may result in neurological conditions possibly including the migraine headache complex. While antioxidants and antioxidant enzymes may be protective, there is also potential for hormones and natural substances to be beneficial and these therapeutic categories may be effectively combined to achieve the best outcomes. In addition to excess free radicals, acute and chronic inflammatory reactions also contribute to the spectrum of injury. Therefore, while many sources may cause injury, only a few common mechanisms are involved. This provides the current invention an opportunity to eliminate or reduce the impact of migraine headache by employing the benefits of antioxidants, hormones, phytochemicals and additional nutrients.

While a standard "Western" diet can promote normal growth and development, foods may also contain naturally occurring toxic as well as protective substances, and the relative levels of these competing elements may be critical. Mutagens and carcinogens are formed during digestion and studies suggest that vitamin C and E consumption reduces the formation of mutagens in the small intestine during this process with the combination of the two being more effective than each antioxidant individually. These antioxidant vitamins are included in the present formulation.

With this background, it is the intent of the current invention to expand the previous application relative to ketogenic sources and the beneficial impact they have on the migraine headache spectrum. These complex formulations aim to maximize the potential health effects beyond ketogenesis alone by combining a broader platform of micronutrients from multiple sources including phytochemicals from plant herbals and their derivatives, vitamins, antioxidants, minerals and other nutrients. It was developed for wide human use from age twelve years and older. The formulation is intended to reduce portions of the initiating and sustaining causes of migraine headache including oxidative damage and inflammation while potentially enhancing neuroprotection.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

The invention relates to migraine headaches, sometimes simply called migraine. More particularly, the invention relates to preventing or reducing the frequency of migraine onset and reducing migraine symptoms. The invention provides effective, safer treatments to reduce frequency of migraine onset. The present inventors have surprisingly discovered that providing KMCT to patients suffering from frequent migraine attacks can reduce frequency of migraine onset and reduce migraine symptoms, without the side effects of medications currently used for this purpose. KMCT are metabolized in the liver to provide a rich source of ketone bodies, which can be metabolized as a carbon and energy source for the body, especially the brain. Unlike ketogenic dieting, providing exogenous KMCT does not result in reduced glucose concentrations or other physiological effects associated with ketogenic dieting, and does not suffer from similar patient compliance issues.

In one embodiment, the method comprises providing the migraineur with dietary KMCT. In some embodiments, the KMCT comprise a mixture of capric and caprylic triglycerides. In some embodiments the KMCT are enriched or purified from coconut oil. In some embodiments the KMCT comprise a mixture of capric and caprylic triglycerides and coconut oil. In some embodiments, the total KMCT provided to the migraineur is from about 3 g to about 30 g/day. In some embodiments, the total KMCT provided to the migraineur is from about 3 g to about 15 g/day.

In another embodiment, the method comprises providing the migraineur with dietary KMCT. In some embodiments, the KMCT comprise a mixture of capric and caprylic triglycerides. In some embodiments the KMCT are enriched or purified from coconut oil. In some embodiments the KMCT comprise a mixture of capric and caprylic triglycerides and coconut oil. In yet another embodiment, the total KMCT provided to the migraineur is from about 3 g to about 30 g/day. In still another embodiment, the total KMCT provided to the migraineur is from about 10 g to about 30 g/day.

In a further embodiment, the method comprises providing the migraineur with dietary KMCT in combination with a pharmaceutical agent provided to reduce the frequency of migraine onset in a migraineur. Such augmentation of pharmaceutical intervention may reduce the dosage and/or frequency of pharmaceutical agent required, thereby reducing unwanted side effects caused by the pharmaceutical agent. In another embodiment, the KMCT comprise a mixture of capric and caprylic triglycerides. In still yet another embodiment, the KMCT are enriched or purified from coconut oil. In some embodiments the KMCT comprise a mixture of capric and caprylic triglycerides and coconut oil. In a further embodiment, the total KMCT provided to the migraineur is from about 3 g to about 30 g/day. In still a further embodiment, the total KMCT provided to the migraineur is from about 3 g to about 15 g/day. Pharmaceutical agents useful in this aspect of the invention include, without limitation, one or more of beta blockers, calcium channel blockers, tricyclic antidepressants, anticonvulsants (such as Depakote and Topamax), and Botox.

In another further embodiment, the method comprises providing the migraineur with dietary KMCT in combination with a pharmaceutical agent provided to reduce migraine symptoms experienced by a migraineur. Such augmentation of pharmaceutical intervention may reduce the dosage and/or frequency of pharmaceutical agent required, thereby reducing unwanted side effects caused by the pharmaceutical agent. In yet another further embodiment, the KMCT comprise a mixture of capric and caprylic triglycerides. In still another further embodiment, the KMCT are enriched or purified from coconut oil. In still yet another further embodiment, the KMCT comprise a mixture of capric and caprylic triglycerides and coconut oil. In another further embodiment, the total KMCT provided to the migraineur is from about 3 g to about 30 g/day. In another embodiment, the total KMCT provided to the migraineur is from about 10 g to about 30 g/day. Pharmaceutical agents useful in this aspect of the invention include, without limitation, one or more of aspirin, acetaminophen, non-steroidal anti-inflammatory drugs (NSAIDs, such as ibuprofen and naproxen), triptans (such as sumatriptan (Imitrex), rizatriptan (Maxalt), almotriptan (Axert), naratriptan (Amerge), zolmitriptan (Zomig), frovatriptan (Frova) and eletriptan (Relpax)), ergotamines (such as Ergotamine and Dihydroergotamine), opioid medications, and glucocorticoids (such as prednisone and dexamethasone).

In a further embodiment, the method comprises providing the migraineur with dietary KMCT in combination with a non-pharmaceutical intervention or agent. In another embodiment, the KMCT comprise a mixture of capric and caprylic triglycerides. In yet another embodiment, the KMCT are enriched or purified from coconut oil. In some embodiments the KMCT comprise a mixture of capric and caprylic triglycerides and coconut oil. In still another embodiment, the total KMCT provided to the migraineur is from about 3 g to about 30 g/day. In still yet another embodiment, the total KMCT provided to the migraineur is from about 3 g to about 15 g/day. Non-pharmaceutical interventions and agents include, without limitation, one or more of transcutaneous electrical nerve stimulation, transcranial magnetic stimulation, biofeedback, acupuncture, cognitive behavior therapy, ketogenic dieting, butterbur extracts, feverfew, L-cysteine, riboflavin, coenzyme-Q supplements, magnesium supplements, tocopherols (vitamin E), calciferols (vitamin D), ascorbic acids and omega fatty acids.

In another further embodiment, the method comprises providing the migraineur with dietary KMCT in combination with a non-pharmaceutical intervention or agent. In yet another further embodiment, the KMCT comprise a mixture of capric and caprylic triglycerides. In still another further embodiment, the KMCT are enriched or purified from coconut oil. In some embodiments the KMCT comprise a mixture of capric and caprylic triglycerides and coconut oil. In still yet another further embodiment, the total KMCT provided to the migraineur is from about 3 g to about 30 g/day. In a further embodiment, the total KMCT provided to the migraineur is from about 10 g to about 30 g/day. Non-pharmaceutical interventions and agents include, without limitation, one or more of caffeine, melatonin, magnesium, feverfew, butterbur, willow extract, ginger, valerian, coriander seed, dong quai root, rosemary, linden, honeysuckle, mullien, yarrow, wintergreen evadia, tocopherols (vitamin E), calciferols (vitamin D), ascorbic acids and omega fatty acids.

In another embodiment, a method for preventing or reducing the frequency of onset of migraine, and/or reducing migraine symptoms, comprises providing a migraineur with dietary ketone esters, ketone salts or other sources of ketone bodies. In one embodiment, the ketone esters or ketone salts are provided in an amount to raise plasma levels of ketone bodies (acetoacetate and [3-hydroxybutyrate) to from about 2 mM to about 5 mM. In another embodiment, the ketone esters and ketone salts include, without limitation, [3-hydroxybutyrate-1,3-butanediol monoester, glyceryl-tris-3-hydroxybutyrate, R-3-hydroxybutyrate-R-1,3-butanediol monoester and D-[3-hydroxybutyrate-(R)-1,3-butanediol. Oral administration of such compounds and determination of plasma levels of resulting ketone bodies for other purposes have previously been described. See e.g., Hashim and Vanitallie, J. Lipid Res. 55: 1818-1826 (2014) and Kashiwaya et al., J. Biol. Chem. 285: 25950-29956 (2010).

For purposes of the invention, the term "in combination with" means administration in any order, including simultaneous administration, as well as temporally spaced order from a few seconds up to several days apart.

Product Formulations

This invention provides novel formulations that are derived from six entirely separate categories of ingredients:

a) Ketogenic Sources
b) Vitamins
c) Minerals
d) Antioxidants
e) Phytonutrients
f) Other Nutrients To provide another enhancement to the unique nature of this invention, different individuals may consume orally or apply to the skin the ingredient levels from the primary standard risk target dosage or from varying doses within the acceptable ranges for one or more of the components. Utilization may also entail none of the ingredients from a category, all the ingredients in a category or partial combinations thereof. The doses listed are intended to be the complete daily dosage. For commercial application in most but not all circumstances, this total dose is intended to be divided in half into two equal servings (generally morning and evening) when consumed or throughout the day as needed when applied to the skin.

For individuals utilizing the "Standard Risk" formulation, it is intended that they consume:

a) at least one of the four ingredients in the "Ketogenic Sources" category
b) at least one of the three ingredients in the "Vitamins" category
c) the ingredient in the "Minerals" category
d) at least one of the three ingredients in the "Antioxidants" category
e) on an optional basis, at least one of the six ingredients in the "Phytonutrients" category
f) on an optional basis, at least one of the three ingredients in the "Other Nutrients" category Category and Ingredient Rationale This section will discuss the scientific rationale for the use of the components of this invention in the major ingredient categories.

Ketogenic Sources:

While ketogenesis and its sources were also addressed in the preceding section, the following is generally applicable to the current invention. Medium chain triglycerides (MCTs) consist of fatty acids with a 6-12 aliphatic carbon atom

TABLE 1

| STANDARD FORMULATION (ages 12 years and older) | | |
|---|---|---|
| | Primary Dose | Range |
| Ketogenic Sources | | |
| Medium chain triglycerides (coconut/palm, capsule) | 5 grams | (1-30 grams) |
| Medium chain triglyceride oil (caprylic, capric acids) | 15 grams | (5-50 grams) |
| (powder) | 4 grams | (1-20 grams) |
| Coconut oil extracts (caproic, caprylic, capric, lauric acids) | 20 grams | (10-50 grams) |
| Ketone salts/esters | 25 grams | (5-60 grams) |
| Vitamins | | |
| B2 (riboflavin, yeast source) | 4 mg | (2-400 mg) |
| B3 (niacinamide ascorbate, nicotinic acid, yeast source) | 20 mg | (5-30 mg) |
| (nicotinamide riboside, nicotinamide adenine dinucleotide) | 300 mg | (50-2000 mg) |
| B6 (pyridoxine hydrochloride, yeast source) | 5 mg | (1-50 mg) |
| Minerals | | |
| Magnesium (citrate, lactate, gluconate, oxide, carbonate, hydroxide, chloride, sulphate, lactic acid, Jay phosphate, tribasic phosphate, natural form) | 300 mg | (50-500 mg) |
| Antioxidants | | |
| Vitamin C (ascorbate salts/acidic form, citrus, rose, berry source) | 500 mg | (100-2000 mg) |
| Vitamin E (vegetable, wheat germ products, natural tocopherol) | | |
| (d-alpha tocopheryl succinate) | 200 IU | (50-400 IU) |
| (d-alpha tocopheryl acetate) | 100 IU | (25-200 IU) |
| Coenzyme Q10 (ubiquinone, organ meat or natural ingredient sources-e.g. *Agrobacterium tumefaciens*, *Paracoccus denitrificans*, *Pseudomonas aeruginosa*) | 60 mg | (5-250 mg) |
| Phytonutrients | | |
| Basil (oil, extract, plant form) | 2000 mg | (500-5000 mg) |
| Butterbur | 100 mg | (25-200 mg) |
| Feverfew (Parthenolides-standardized 0.2-0.4%, tea, leaves) | 400 mg | (100-1200 mg) |
| (carbon dioxide, extract) | 100 mg | (5-400 mg) |
| Ginger (gingerol, root, tea, oil, powder) | 500 mg | (50-2000 mg) |
| Peppermint (extract, gel, liquid, chewable, enteric-coated, capsule) | 100 mg | (50-1000 mg) |
| Valerian (root, tea, extract, powder, plant source) | 250 mg | (100-1200 mg) |
| Other Nutrients | | |
| Melatonin (hormone, solid, liquid) | 3 mg | (0.1-10 mg) |
| Caffeine | 125 mg | (25-250 mg) |
| Peppermint (essential oil-10% solution) | 0.5 ml | (0.1-1.5 ml) |

chain. This specific group of four predominant fatty acids are directly metabolized to ketone bodies that provide alternative cellular energy sources especially to neurons. They are naturally sourced from coconut and palm oils and are generally more effectively ketogenic, rather than longer chain triglycerides which are usually not. Therefore, the interest in diets utilizing this biologic mechanism has flourished dramatically and the term "Ketonomics®" has been proprietarily ascribed to the underlying science. MCT-containing oils can improve liver and cardiovascular function in obesity-related metabolic syndrome in vivo. These compounds may also experimentally provide reduction in harmful inflammatory responses. Increasing research has suggested possible beneficial effects of MCTs in neurological conditions such as dementias, seizure disorders and migraine headaches. There is also recent evidence of an anti-cancer effect from MCT-supplemented diets in mice. In addition, these triglycerides may reduce food intake through thermogenesis and positively impact obese subjects.

Vitamins

Vitamin B2

Vitamin B2 or riboflavin is a critical water-soluble member of the B vitamin family in humans. It is important in energy production, neural health, immune system function and plays a vital role in several key enzymatic reactions. Chemoprevention is noted at high doses and deficiency increases the risk of cancer. It also assists in regulation of homocysteine levels, thereby supporting cardiovascular health and is involved in iron metabolism reducing anemia risk. Finally, this compound can function as an antioxidant to decrease oxidative stress, lipid peroxidation and tissue reperfusion injury. It has neurological properties related to this invention, including increasing myelin formation, enhancing mitochondrial function and is neuroprotective against migraine headache, Parkinson's disease and multiple sclerosis while providing visual protection against glaucoma. Most specifically, vitamin B2 is important in lowering stress, mood changes, anxiety and depression, and therapeutically, reduces frequency and duration of migraine headache while decreasing the need for other migraine medications. Its consumption is remarkably safe even at high treatment dosages.

Vitamin B3

The complex referred to as vitamin B3 comprises niacin, niacinamide and nicotinamide riboside (NR). These forms all produce the compound, nicotinamide adenine dinucleotide (NAD), that is critical for human metabolism, cellular function, transfer reactions and DNA repair. NR is particularly effective for this purpose. NAD is a requisite in enabling cells to produce energy in the mitochondria and works synergistically with other energy sources in the Kreb's cycle including ketones. It is also an important substrate for NAD-consuming enzymes including the sirtuins, that have potential beneficial effects on aging and circadian rhythms, and poly ADP-ribose polymerases, a family of proteins involved in essential cellular functions including genomic stability, DNA repair and programmed cell death, or apoptosis.

Extensive research studies show that NAD levels decrease with advancing age and under metabolic stress. Supplementation of NR has been demonstrated to help support many aspects of healthy aging, including cardiovascular and brain health. It also helps generate energy in mitochondrial-dense tissues like muscle, brain, and liver. NR has achieved GRAS (generally recognized as safe) status in the United States as a food ingredient in nutritional products.

Vitamin B6

The most important functions of vitamin B6, pyridoxine, are related to the health of the nervous and immune systems. Specifically, this vitamin is involved in the biosynthesis of neurotransmitters thereby impacting cognitive development. Deficiency is associated with several clinical conditions resulting in low plasma concentrations. Although there have limited effects in other conditions, relative to this invention, adequate levels have shown health benefits in neurocognitive domains.

Minerals

Magnesium

Magnesium holds a prominent position among essential elements that function as required co-factors for critical enzymatic reactions, biochemical function and metabolic pathways. It is found in all body tissues including the brain and can improve bone health, stabilize blood pressure, and help maintain a normal cardiac rhythm and nerve function. Magnesium deficiency may result in fatigue, loss of appetite, nausea, muscle cramping, tingling, muscle contractions and is linked to migraine headache. Many people do not receive enough magnesium in their diet but supplementation of the mineral is generally safe and is an effective therapeutic intervention in many clinical situations. It may also have a role as an electrolyte. One of the prime targets of migraine therapy is control of pain and this mineral has been shown to be beneficial by extensive analysis of human clinical trials in modulation of pain perception inclusive of severe headache. In addition, magnesium supplementation has further demonstrated its clinical efficacy and broad potential applications as it can provide preventive symptom effects and reduce complications in surgical conditions.

Several studies support the use of this mineral in migraine sufferers since low levels of magnesium are found in half of those migraineurs especially during attacks. Oral and intravenous supplementation may reduce the frequency and severity by more than 40 percent. Magnesium combinations with other nutrients in this invention such as vitamin B2 and co-enzyme Q-10 have shown similar benefits without adverse events during prolonged treatment periods.

Antioxidants

Glutathione, a sulfhydryl compound, is the body's primary endogenously formed antioxidant. The importance of intracellular glutathione is well known and its defense of the immune system as well as relevance to neurologic pathophysiology is being increasingly recognized.

It can catabolize anions and hydrogen peroxide and is a potent intracellular protective agent against excess free radical damage. In addition, sulfhydryl compounds protect against radiation injury to the bone marrow and gastrointestinal system as well as against cellular mutagenesis and can induce radiation resistance. However, while potentially preferred, when glutathione is consumed orally by humans, its plasma levels do not significantly increase suggesting that this tripeptide is completely hydrolyzed in the intestinal tract during digestion. Therefore, this invention utilizes alternative antioxidants to provide these benefits relative to migraine headache.

Vitamins C and E

Reducing oxidative damage and inflammation are important aspects to protecting against migraine headache. Vitamin C prevents lipid oxidation and potentiates nitric oxide activity in normalizing vascular function in patients with a variety of diseases and associated high risk exposures. Vitamin C is necessary to protect cellular components in aqueous environments and plays an important role in maintaining cellular levels of vitamin E by recycling the vitamin E radical (oxidized) to the reduced (antioxidant) form. Recent studies have elucidated the metabolic and genetic cellular mechanisms in hematopoietic stem cells where mutations can lead to blood disorders. Vitamin C appears to restore normal cellular regulation and may reduce cancer risk and progression. Vitamin C as calcium ascorbate is beneficial because it is the most effective non-acidic form available for human use and, therefore, is less likely to cause stomach upset, diarrhea, and other issues than the ascorbic acid form. The combination of vitamins C and E produces a synergistic inhibition on LDL-cholesterol oxidation.

In addition to functioning as a robust antioxidant, vitamin E is protective in reducing oxidation of membrane-bound cholesterol, c-myc activated pathways responsible for smooth muscle cell proliferation and aggregation of platelets. However, the proper form, ratio and type of vitamin E are important to maximize the reduction of oxidative damage. Not all forms of the vitamin are easily soluble and can enter cells. Human tissues selectively absorb the natural form of vitamin E, d-alpha tocopherol, which acts in the intestinal tract and in the extracellular space and can stimulate the immune system. The d-alpha tocopheryl succinate form of vitamin E is the most effective natural form of this micronutrient to maintain internal cellular components and also shows active antioxidant effect by reducing the incidence of radiation-induced transformation in vitro. This form of vitamin E is a more effective antioxidant than the alpha tocopherol or other mixtures of tocopherols.

Multiple antioxidants are more effective than the individual agents themselves. For example, a combination of antioxidants is more effective in tumor cell growth inhibition than any of the individual agents utilized. Vitamin C and vitamin E are synergistic as antioxidants against free radicals because they protect both the aqueous and lipid environments of the cells respectively and, thus, are recommended to be used in combination in the current invention. In this regard and relevant to this invention, these antioxidants and others have been shown to be effective radioprotectants. Additional antioxidant combinations can protect against ischemia and reperfusion injury. It is also recognized that oxygen level may vary widely within organs, tissues and individual cells. This is especially true during the biological damage related to adverse health such as migraine headache as addressed by this invention. Compared to other antioxidants, vitamin E maintains its effect even at reduced oxygen pressures.

Co-Enzyme Q-10

Another adjunctive agent in this formulation is co-enzyme Q-10 (CoQ10), or ubiquinone. CoQ10 has demonstrated antioxidant properties albeit less potent ones than with the substances previously described. A fat-soluble compound, it is relevant to this invention because it acts as a co-factor for generating adenosine-5'-triphosphate (ATP) during Kreb's cycle metabolism, thereby, generating energy primarily in the mitochondria, including in the brain. This is particularly important in neurological conditions such as migraine headache where improvement in mitochondrial function can result in improved energy levels and quality of life. CoQ10 is active in electron transport mechanisms and cellular oxygen uptake. Its free radical-scavenging qualities are likely responsible for some of the reported beneficial effects with various cardiovascular symptoms and neurological conditions. In addition, CoQ10 can more directly protect against several neurological abnormalities. Finally, this compound scavenges peroxy radicals faster than alpha-tocopherol and, like vitamin C, can regenerate vitamin E in a redox cycle.

Phytonutrients:

Basil Oil

Basil oil (*Ocimum basilicum*), is considered in traditional herbal medicine as an adaptogenic herb which helps restore balance and energy in the human body. Adaptogenic herbs have long been used in combating stress-related health problems, including headaches and migraines. Many headaches and migraines are caused by stress, with a reduction in cortisol helping to reduce their severity. According to the Journal of Agriculture and Food Chemistry, basil oil provides both antimicrobial and antioxidant functions. Because basil is a muscle relaxant, it can relieve tension headaches with its analgesic qualities.

Butterbur

Butterbur (*Petasites hybridus*) has been used in its purified root extract form as an herbal pill supplement to treat headaches and migraines. A 2012 study published in Neurology supports conclusions from older studies that Petasites is effective for migraine prevention when taken within the dosage ranges as provided in the standard formulation of the current invention. The butterbur extract (petasin) is the only natural supplement listed as having Level A evidence by the American Headache Society and American Academy of Neurology in their 2012 migraine prophylaxis guidelines. The report concludes that butterbur is "established as effective and should be offered for migraine prevention."

While the exact mechanism of action is unknown, petasins appear to have calcium-channel-blocking effects that may contribute to the efficacy of butterbur root. Laboratory data also demonstrates butterbur's anti-inflammatory and vasodilatory effects on the cerebral arteries via inhibition of the lipoxygenase pathway and leukotriene synthesis.

In early trials for migraine prophylaxis, patients consuming butterbur for two months did not report any migraine attacks during the treatment phase while patients in the placebo group continued to suffer at least one migraine headache during the same period. This effect may be due to the herb's anti-inflammatory and spasmolytic (muscle-relaxant) effects. Butterbur contains active components known as isopetasin, oxopetasin, and petasin, which induce smooth muscle relaxation, particularly in cerebral blood vessel walls. Petasin also inhibits the proinflammatory enzyme, lipoxygenase (LOX), while both petasin and isopetasin exert highly potent anti-inflammatory effects by inhibiting leukotriene synthesis. Butterbur extract has been reported to inhibit cyclooxygenase-2 (COX-2) activity which relieves pain and inflammation. In addition, petasins decrease the intracellular concentration of calcium, thus offsetting calcium-induced vasoconstriction, which may account for the potent anti-inflammatory and spasmolytic effects.

There have been reported potential safety concerns relative to the manufacturing process of butterbur in Europe. It appears that unprocessed, or unpurified, butterbur may contain pyrrolizidine alkaloids, which are known to be hepatotoxic, mutagenic, and carcinogenic. Careful attention must be given to the control of these alkaloids to assure that they are completely removed. However, current extracts that are prepared for human use as employed in this invention are processed to remove these alkaloids. An independent evaluation of data gathered from various trials concluded that commercially marketed butterbur root extract is entirely safe for human consumption. A standardized butterbur extract has been used by more than half a million German citizens since its introduction in 1988, with reportedly acceptable the safety data.

Feverfew

Feverfew (*Tanacetum parthenium*) has been traditionally used in Eastern European cultures for headaches, insect bites, and other pain. Recent studies suggest that feverfew is an effective treatment for migraines and may be useful as a preventative strategy. Indeed, rigorous systematic reviews noted benefit in three of five clinical trials.

The neurotransmitter serotonin (5-hydroxytryptamine [5-HT]) plays a role in the development of migraine attacks with migraineurs tending to have low cerebral serotonin levels. Although the exact mechanism that links abnormal 5-HT neurotransmission to the manifestation of headache is not fully understood, a deficit in the 5-HT descending pain inhibitory system is probably the most implicated in migraine pathophysiology. It has been suggested that parthenolide may be a low-affinity antagonist at 5HT2A receptors. Drugs that are serotonin receptor antagonists are used in migraine prevention and experimental studies have shown that parthenolide, as well as other sesquiterpene lactones inhibits serotonin release. More than 30 sesquiterpene lactones have been identified in feverfew. Members of this class have been isolated and possess spasmolytic activity, perhaps through an inhibition of the influx of extracellular calcium into vascular smooth muscle cells. A proposed mechanism of anti-inflammatory activity of feverfew involves parthenolide specifically binding to and inhibiting IκB kinase complex (IKK)β. IKKβ plays an important role in pro-inflammatory cytokine-mediated signaling. Feverfew's prophylactic action for migraine may also involve other mechanisms including inhibition of prostaglandin synthesis, decrease of vascular smooth muscle spasm, and blockage of platelet granule secretion.

The current invention presents a standard formulation that incorporates effective primary target dosages and dose ranges for the various forms of feverfew based on available scientific reports for both prophylaxis and treatment.

Ginger

The ginger (*Zingiber officinale*) plant has long been used in traditional Chinese, Indian and Arabic herbal medicine. It has known anti-inflammatory effects and in human trials has been shown to reduce muscle discomfort associated with physical activity. The herb has compared favorably to pharmaceutical drugs for migraine therapy especially in regard to control of nausea and vomiting which often accompany the headache as well as minimizing side effects of treatment. Ginger contains the powerful phenol, gingerol, and the active chemical, zingerone that are responsible for a portion of its strong effect. In addition, the more than 200 essential oils or extracts of this phytonutient have shown antihistaminic and radioprotective properties. In fact, this agent can produce decreases in inflammation biomarkers and muscle soreness in both male and female subjects. Ginger also exhibits a neuroprotective in vivo effect by enhancing the antioxidant defense mechanisms in the brain. Many of these mechanisms of action may contribute to the efficacy related to migraine headache.

Peppermint

Peppermint (*Mentha×balsamea*) represents a hybrid combination of spearmint and water mint that grows throughout North America, Europe, and Asia. This ingredient is provided in the current invention in two separate categories depending on its method of utilization. Oral consumable forms (liquid, chewable) as well as gel-based or enteric-coated capsules have been ingested for a variety of conditions. In addition, a 2010 study published in the International Journal of Clinical Practice found that a ten percent solution of menthol, the active ingredient in peppermint, was effective at terminating migraine pain and easing nausea when applied topically to the forehead and temples. Thus, peppermint may be considered an effective herbal option for the relief of migraine pain. The ingested ingredient form is categorized as a "Phytonutrient" in this invention while the essential oil form (applied to the skin) is listed as an "Other Nutrient".

The rationale for using peppermint to alleviate headache is based on several assumptions. Relative to peppermint oil, certain analgesic mechanisms have been recently described. Local application of peppermint oil generates a long-lasting cooling effect on the skin, caused by a steric alteration of the calcium channels in cutaneous cold-receptors. Further it was shown that peppermint oil inhibits non-competitively 5-hydroxytryptamine (serotonin) and substance P-induced smooth muscle contraction in animal models. A significant analgesic effect with a reduction in sensitivity to headache can also be produced by the combination of peppermint oil and ethanol. The essential plant oil preparations are shown by laboratory tests to exert significant effects on mechanisms associated with the pathophysiology of clinical headache syndromes.

Valerian (*Valeriana officinalis*), has been a remedy for insomnia for centuries. Valerian was known as "all-heal" in the 1500s, as it was used to treat a multitude of ailments. It is now used in the modern treatment of headaches. It is not known how valerian works to ease migraine symptoms in some sufferers. Many of the compounds present in valerian are believed to have sedative and relaxing effects. Its activity may result from interactions among multiple constituents rather than any one compound or class of compounds. Its content includes volatile oils, including valerenic acids, the less volatile sesquiterpenes, and the valepotriates (esters of short-chain fatty acids). This combination may lead to the relief of migraine headache symptoms. The positive effect of valerian capsules in patients with migraine attacks treated with sodium valproate was assessed in a randomized human clinical trial.

Phytonutrient Interactions and Risks

It is known that some phytonutrients have potential for adverse health effects including oxidative stress, liver toxicity, increased bleeding risk (individuals taking blood thinners) and interference with some prescription medications. The incidence of risk for the phytonutrients utilized in this invention are rare and usually noted in association with uncontrolled consumption or contamination with microbials, mycotoxins or heavy metals, and not as a causative agent of the observed health effect. Nevertheless, whenever these ingredients are included in a formulation, appropriate statement for referral to a health care professional for product approval is suggested.

Other Nutrients

Melatonin

The pineal gland hormone, melatonin, is another antioxidant that has demonstrated protective qualities against hazardous exposures in laboratory, in vivo and in clinical studies with particular relevance to the current invention. It induces sleep and can improve exercise tolerance, energy and performance. Sleep duration is increasingly being recognized as important in regards to chronic disease prevention. The hormone effectively crosses the blood-brain barrier, increases brain antioxidants and decreases swelling, inflammation and pressure in concussive head injury models. Since migraines may be caused in part by changes in the brainstem or chemical imbalances in the brain, sleep pattern alteration has been shown to trigger migraines in some people. There are several thoughts that have emerged to suggest that melatonin plays a role in a variety of headache disorders, including migraine, cluster, and tension. For example, melatonin levels change in patients suffering from some types of headaches. In migraineurs, melatonin levels are lower on days when attacks occur compared with the days when they do not. Patients with chronic migraine also appear to have lower melatonin levels than those with episodic migraine. Nighttime melatonin levels are also lower in migraine sufferers compared with others. Prospective, placebo-controlled clinical trials assessing the use of melatonin for migraine prevention have produced mixed findings. While crossover trials have not shown a migraine frequency difference, abnormally low urinary melatonin byproduct levels were consistently found in chronic migraineurs, suggesting a potential therapeutic pathway. A more promising study published in the journal Neurology found that daily melatonin helped reduce the frequency of migraines. Melatonin therapy also experientially appeared to reduce the length of migraine attacks, as well as the severity and was effective in reducing the number of headache days per month with minimal adverse effects.

Caffeine

Caffeine has important potential roles in migraine headache therapeutics, either alone or in combination with other modalities and demonstrates favorable tolerability. Because it contains "vasoconstrictive" properties that cause the blood vessels to narrow and restrict blood flow, caffeine can aid in head pain relief. Combinations of caffeine with analgesic medications, including acetaminophen, acetylsalicylic acid, and ibuprofen, showed significantly improved efficacy in the treatment of patients with migraine compared with analgesics alone. Among other positive effects are benefits in sleep pattern improvement which is a significant necessity for many migraine sufferers. If individuals are at all sleep-deprived, caffeine may influence alertness, recovery sleep and mental fatigue. In this setting, it may also improve functional performance and decrease pain perception. However, it must be noted that caffeine withdrawal and caffeine intake can also be potential triggers for headaches and migraines. Of additional relevance to this invention, dark chocolate, which may be a flavoring component in the present formulation, contains not only caffeine but large amounts of magnesium (see discussion in previous section on "Minerals").

Impact of the Invention:

Research demonstrates that less than ten percent of oral micronutrients are usually fully absorbed. Thus, the dosages and dose ranges must have wide applicability. It appears rational to utilize several formulation categories containing the basic nutrients that impact migraine headache and then blend the combinations of ingredients for optimal effect. In this invention, for those components that are ingested, the primary dosing and ranges are designed to be at adequately broad and at sufficient levels to have the desired beneficial effects in humans of both genders and of wide age and weight cohorts. The basic classes of nutrients to which the components of the present invention belong are known to reduce oxidative damage and inflammation, support neuroprotection and, thereby, provide benefit to sufferers of migraine headache.

While the current product platform describes oral capsules and essential oils applied to the skin, this invention is intended to also relate to any form of administration of these formulations in humans including but not limited to tablets, bars, liquids, powders, gummies, lozenges/troches, dissolvable disks, chewables, inhalational forms, injectables, patches, ointments, gels, aerosols and sticks as well as any transcutaneous, intranasal, intra-cavitary, liposomal, nanotechnology or other delivery system.

What is claimed is:

1. A formulation comprising at least one ketogenic source from about 1 to about 60 g, at least one vitamin from about 1 to about 2,000 mg, at least one mineral from about 50 to about 500 mg, at least one antioxidant from about 5 to about 2,000 mg, at least one phytonutrient from about 5 to about 5,000 mg, and at least one nutrient from about 0.1 to about 250 mg, said at least one ketogenic source is selected from the group consisting of medium chain triglycerides, coconut capsule, palm capsule, medium chain triglyceride oils, caprylic acid, capric acid, medium chain triglyceride powder, coconut oil extracts, caproic acid, lauric acid, ketone salts, ketone esters, and mixtures and combinations thereof said at least one vitamin is selected from the group consisting of Vitamin B2, Vitamin B3, nicotinamide riboside, nicotinamide adenine dinucleotide or vitamin B6, said at least one mineral is selected from the group consisting of magnesium citrate, magnesium lactate, magnesium gluconate, magnesium oxide, magnesium carbonate, magnesium hydroxide, magnesium chloride, magnesium sulphate, tribasic phosphate, and mixtures and combinations thereof, said at least one antioxidant is selected from the group consisting of Vitamin C, ascorbate salts, citrus, rose, berry source, Vitamin E, vegetable products, wheat germ products, natural tocopherol, d-alpha tocopheryl succinate, d-alpha tocopheryl acetate, Coenzyme Q10, ubiquinone, organ meat, natural ingredient sources, *Agrobacterium tumefaciens, Paracoccus denitrificans, Pseudomonas aeruginosa*, and mixtures or combinations thereof, said phytonutrients are selected from the group consisting of basil, butterbur, feverfew, ginger, peppermint, Valerian, and mixtures and combinations thereof, and said nutrients are selected from the group consisting of melatonin, caffeine, peppermint essential oil, and mixtures and combinations thereof.

2. The formulation of claim 1 wherein said formulation is utilized to treat, prevent, and relieve the symptoms of a migraine headache.

* * * * *